US007223334B2

(12) United States Patent
Okamoto et al.

(10) Patent No.: US 7,223,334 B2
(45) Date of Patent: May 29, 2007

(54) SEPARATING AGENT FOR ENANTIOMERIC ISOMERS

(75) Inventors: Yoshio Okamoto, Aichi (JP); Chiyo Yamamoto, Aichi (JP); Takateru Kubota, Aichi (JP)

(73) Assignee: Daicel Chemical Industries, Ltd., Sakai-shi, Osaka (JP)

( * ) Notice: Subject to any disclaimer, the term of this patent is extended or adjusted under 35 U.S.C. 154(b) by 317 days.

(21) Appl. No.: 10/936,846

(22) Filed: Sep. 9, 2004

(65) Prior Publication Data

US 2005/0045561 A1    Mar. 3, 2005

Related U.S. Application Data

(62) Division of application No. 10/258,706, filed as application No. PCT/JP02/02137 on Mar. 7, 2002, now abandoned.

(30) Foreign Application Priority Data

Mar. 7, 2001    (JP)    ............................... 2001-63001

(51) Int. Cl.
    *B01D 15/08*    (2006.01)
(52) U.S. Cl. ............................... 210/198.2; 210/502.1; 210/635; 210/656; 502/404
(58) Field of Classification Search ............ 210/635, 210/656, 198.2, 502.1; 502/404; 95/88; 96/101
    See application file for complete search history.

(56) References Cited

U.S. PATENT DOCUMENTS

| | | | | |
|---|---|---|---|---|
| 4,786,415 | A | | 11/1988 | Shibata et al. ............ 210/198.2 |
| 4,818,394 | A | | 4/1989 | Okamoto et al. .......... 210/198.2 |
| 5,030,354 | A | | 7/1991 | Miwa et al. .............. 210/198.2 |
| 5,192,444 | A | | 3/1993 | Shibata et al. ............ 210/198.2 |
| 5,207,914 | A | * | 5/1993 | Lin ............................. 210/635 |
| 5,357,001 | A | * | 10/1994 | Grosse-Bley et al. .... 525/326.1 |
| 5,868,938 | A | * | 2/1999 | Bomer et al. ............... 210/656 |
| 2003/0141252 | A1 | * | 7/2003 | Okamoto et al. ........... 210/656 |

FOREIGN PATENT DOCUMENTS

| | | | |
|---|---|---|---|
| EP | 147 804 | 7/1985 | .............. 210/198.2 |
| EP | 0 157 364 | 9/1990 | .............. 210/198.2 |
| JP | 57-150432 | 9/1982 | .............. 210/198.2 |
| JP | 60-142930 | 7/1985 | .............. 210/198.2 |
| JP | 63-307829 | 12/1988 | .............. 210/198.2 |
| JP | 5-51327 | 3/1993 | .............. 210/198.2 |
| JP | 5-239103 | 9/1993 | .............. 210/198.2 |
| JP | 6-71170 | 3/1994 | .............. 210/198.2 |

OTHER PUBLICATIONS

Journal of the American Chemical Society, *Useful Chiral Packing Materials for High-Performance Liquid Chromatographic Resolution of Enantiomers: Phenylcarbamates of Polysaccharides Coated on Silica Gel*, 1984, pp. 5357-5359.
Pharm Tech Japan, *Separation of Chiral Compounds*, vol. 12, No. 1 (1996) pp. 43-52.
Soc. of Synthetic Organic Chemistry, *Liquid Chromatographic Resolution of Optical Isomers—Development and Characteristics of Chiral Staionary Phases Consist of Polysaccharide Derivatives and Application to Large Scales Separtion*, 1996, pp. 344-353.
Polymer Preprints, Japan, vol. 49, No. 13, 2000, cover page and pp. 4042-4043 and bibliographic page, with English translation.
Tris (cyclohexylcarbamate) s of Cellulose and Amylose as Potential Chiral Stationary Phases for High-Performance Liquid Chromatography and Thin-Layer Chromatography, by T. Kubota et al, J. Am. Chem. Soc., vol. 122, No. 17, 2000, pp. 4056-4059.

* cited by examiner

*Primary Examiner*—Ernest G. Therkorn
(74) *Attorney, Agent, or Firm*—Flynn, Thiel, Boutell & Tanis, P.C.

(57) ABSTRACT

The present invention provides a separating agent for enantiomeric isomers having no large UV absorption, as represented by an aromatic group, and having high asymmetric recognizability, particularly, high asymmetric recognizability in an aqueous mobile phase, or a separating agent for enantiomeric isomers containing a polysaccharide alicyclic ester derivative free from an aromatic group as an effective component.

8 Claims, No Drawings

SEPARATING AGENT FOR ENANTIOMERIC ISOMERS

This is a division of Ser. No. 10/258,706, filed Oct. 25, 2002, now abandoned which was the national stage of International Application No. PCT/JP02/02137, filed Mar. 7, 2002, which International Application was not published in English.

TECHNICAL FIELD OF THE INVENTION

The present invention relates to a separating agent for enantiomeric isomers, in particular, a separating agent suitably used for separating enantiomeric isomers in chromatography. More particularly, the present invention relates to a separating agent for enantiomeric isomers that can enantiomerically resolve many kinds chiral compounds with high separation factors in the analysis of pharmaceuticals, foods, agricultural chemicals, fragrants and the like.

PRIOR ARTS

Many organic compounds have enantiomeric isomers that have the same physical and chemical properties such as boiling point, melting point, solubility and the like but show a difference in the physiological activity that influences the living body of an organism. This difference in the physiological activity between enantiomeric isomers is attributable to the following. In most cases, proteins and carbohydrates that compose the organism are composed only of the one of the enantiomeric isomers so that they show a difference in the manner of action to the other enantiomeric isomer. In the field of pharmaceutical preparations, particularly, in many cases, there are significant differences in medical effect and toxicity between the two enantiomeric isomers. Therefore, in the Guideline for the Production of Pharmaceuticals, the Ministry of Health, Labor and Welfare describes "when the drug of interest is a racemic modification, it is desirable to preliminarily study absorption, distribution, metabolism and excretion kinetics of each enantiomeric isomer."

Since enantiomeric isomers have completely the same physical and chemical properties, they cannot be separated and analyzed by ordinary separation means. Therefore, extensive studies have been made on techniques for easily and precisely separating and analyzing a wide variety of enantiomeric isomers.

As a result, as an analytical technique that meets these requirements, an optical resolution method by high performance liquid chromatography (HPLC), in particular an optical resolution method by using a chiral column for HPLC (chiral stationary phase method) has been developed and widely spread. The chiral column referred to herein means an asymmetry recognition agent itself or a column using, as a filler, a chiral stationary phase composed of an asymmetry recognition agent supported on a suitable carrier.

As such asymmetry recognition agents, for example, optically active poly(triphenylmethylmethacrylate) (c.f., Japanese Patent Application Laid Open No. 57-150432), cellulose and amylose derivatives (Y. Okamoto, M. Kawashima and K. Hatada, J. Am. Chem. Soc., 106, 5337, 1984), ovomucoid, which is a protein (Japanese Patent Application Laid Open No. 63-307829) and the like have been developed. It has been known that among many chiral stationary phases for HPLC, a chiral stationary phase having a cellulose or amylose derivative supported on silica gel has high asymmetry recognition ability to an extremely wide variety of compounds. Furthermore, in recent years, studies on a liquid chromatographic fractionation method for optically active substances in an industrial scale by the combination of the chiral stationary phase for HPLC with a simulated moving bed process have been developed (Pharm Tech Japan, 12, 43 (1996). In order to not only simply perform a base line separation but also further increase productivity of chromatographic fractionation, a chiral stationary phase being capable of further separating a target compound or having as high a value of the separation factor a as possible has been desired.

Since the HPLC chiral stationary phase is frequently used under a reversed phase condition that is an aqueous mobile phase, frequent replacement between an organic solvent-based mobile phase and the aqueous mobile phase is complicated and unsuitable from the point of the maintenance of analytic equipment. It might also lead to a wrong operation by the mixing of the mobile phases. Therefore, it has been desired to perform an analysis in either one of the mobile phase systems, more preferably, in the aqueous mobile phase system. Further, in relation to the recent environmental problems, there is a trend to reduce the organic solvent discharged as mobile phase as much as possible.

As the chiral stationary phases to be used under a reversed phase condition, one using the protein as an asymmetry recognition agent, one using a polysaccharide derivative capable of separating the widest variety of racemic compounds as an asymmetry recognition agent, and the like have been developed and marketed, and an asymmetry recognition agent having further remarkable separation characteristics has been demanded.

Recently, there is growing interest in a thin-layer chromatography (chiral TLC) for enantiomeric isomer separation capable of performing an enantiomeric isomer separation in capillary electrophoresis (CE) field or performing an enantiomeric isomer separation with a separating operation easier than HPLC. The cellulose and amylose derivative-based chiral stationary phases developed and marketed so far as HPLC chiral stationary phase are mostly formed of aromatic derivatives, except an acetate derivative, because it has been considered that the interaction between n-nelectrons plays an important part in the asymmetry recognition between a substituent of a polysaccharide derivative and a solute (Society of Synthetic Organic Chemistry, 54, 344 (1996), Japanese Patent Application Laid Open No. 60-142930). However, an asymmetry recognition agent having a substituent having a large UV absorptive group as an aromatic group had the disadvantage in that it is not applicable to, for example, thin-layer chromatography as described above, liquid chromatographic separation comprising adding the asymmetry recognition agent to a mobile phase, micelle dynamic chromatography that is one kind of capillary electrophoresis, and the like.

This reason is that the UV absorption of an intended substance is relatively minimized so as to be undetectable when a large UV absorption, as represented by the aromatic group, is present in a background (corresponding to a thin layer or mobile phase) in a generally extensively used UV detector. Accordingly, a polysaccharide derivative-based asymmetry recognition agent having high asymmetric recognition ability and minimized UV absorption has been demanded so as to be applicable to the chiral CE field and chiral TLC field.

The present invention thus has an object to provide a separating agent for enantiomeric isomers free from large UV absorption as represented by an aromatic group and having high asymmetry recognition ability, particularly high asymmetry recognition ability in an aqueous mobile phase.

DISCLOSURE OF THE INVENTION

As a result of eager studies for achieving the above-mentioned object, the present inventors have now achieved the present invention.

Namely, the present invention provides a separating agent for enantiomeric isomers comprising a polysaccharide alicyclic ester derivative free from aromatic group as an effective component.

The polysaccharide alicyclic ester derivative free from an aromatic group is specifically cellulose tris(cyclohexylcarboxylate), cellulose tris(cyclopentylcarboxylate) or cellulose tris(cycloadamantylcarboxylate).

The present invention further provides a method for separating enantiomeric isomers by chromatography using a chiral stationary phase containing a polysaccharide alicyclic ester derivative free from an aromatic group as an effective component, or a use for a polysaccharide alicyclic ester derivative free from an aromatic group as a separating agent for enantiomeric isomers.

DETAILED DESCRIPTION OF THE INVENTION

Hereinafter, embodiments of the present invention will be described in detail.

The polysaccharide alicyclic ester derivative free from an aromatic group used in the present invention can be obtained by reacting a polysaccharide with an alicyclic compound having a functional group that is reactive with the hydroxyl group of the polysaccharide to form an ester bond.

The polysaccharide used in the present invention may be any polysaccharide, such as a synthetic or natural one or a modified natural one as long as it has optical activity. The polysaccharide has preferably a high regularity in the manner of binding between saccharides. Examples of the polysaccharide include β-1,4-glucan (cellulose), α-1,4-glucan (amylose or amylopectin), α-1,6-glucan (dextran), β-1,6-glucan (pustulan), β-1,3-glucan (for example, curdlan, schizophyllan, etc.), α-1,3-glucan, β-1,2-glucan (crown gall polysaccharide), α-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose and alginic acid. Also, starches containing amylose are included therein. Among these polysaccharides, it is preferable to use cellulose, amylose, β-1,4-xylan, β-1,4-chitosan, chitin, β-1,4-mannan, inulin, curdlan, etc. which can be easily obtained as highly pure polysaccharides, still preferably cellulose.

It is preferable that such a polysaccharide has a number-average degree of polymerization (i.e., the average number of pyranose or furanose rings per molecule) of at least 5, still preferably, at least 10. From the viewpoint of handling properties, it is preferable that the number-average degree of polymerization thereof is not more than 1,000, though the upper limit thereof is not particularly defined.

As the alicyclic compound having a functional group capable of reacting with the hydroxyl group of the polysaccharide to form an ester bond, which is used in the present invention, any compound may be used as long as it has a functional group capable of forming an ester bond, such as an acid halide having an alicyclic structure free from large UV absorption represented by an aromatic group, or the like. To impart the effect for regularly aligning the polysaccharide derivative frames or substituents, an alicyclic compound having a ring larger than 3-membered ring, more preferably larger than 5-membered ring, or an alicyclic compound having a cross-linking structure is desirable. Particularly preferable examples of the polysaccharide alicyclic ester derivative not having a large UV absorption represented by an aromatic group, which is used in the present invention, include ester derivatives of polysaccharides having at least 0.1 ester bond per glucose unit, particularly, cycloalkylcarboxylates of polysaccharides. Specifically, they include cyclohexylcarboxylate, cyclopentylcarboxylate and cycloadamantylpentylcarboxylate.

The polysaccharide alicyclic ester derivative free from an aromatic group used in the present invention can be formed into an intended separating agent for enantiomeric isomers by either a method for supporting it on a carrier described below or a method for pulverizing or pelletizing the polysaccharide derivative itself.

The supporting referred to herein means that the polysaccharide derivative is fixed on the carrier. The fixation may be performed by any means as physical adsorption between the polysaccharide derivative and the carrier, chemical bonding with the carrier, mutual chemical bonding between polysaccharide derivatives, chemical bonding of a third component, irradiation of the polysaccharide derivative, radical reaction and the like. The carriers referred to herein include porous organic carriers and porous inorganic carriers, and the porous inorganic carriers are preferable. Appropriate examples of the organic porous substrates include polymers comprising polystyrene, polyacrylamide, polyacrylate, etc. Appropriate examples of the inorganic porous substrates include silica, alumina, magnesia, glass, kaolin, titanium oxide, silicates and hydroxyapatite. Silica gel may be cited as a particularly preferable carrier. The particle diameter of the silica gel is preferably from 0.1 µm to 10 mm, and more preferably from 1 µm to 300 µm, and the average pore size thereof is from 10 angstroms to 100 µm, preferably from 50 angstroms to 50,000 angstroms. When silica gel is employed as the carrier, it is preferable to preliminarily surface-coat the silica gel so as to exterminate the effects of the silanol remaining therein, though a non-surface-treated one may be used without any problem.

The amount of the polysaccharide alicyclic ester derivative supported on the carrier is preferably 1 to 100 parts by weight, particularly preferably 5 to 60 parts by weight, based on 100 parts by weight of the carrier.

The pulverization or pelletization of the polysaccharide alicyclic ester derivative may be performed by any known method. The resulting pulverized or spherical polysaccharide derivative is used as it is or desirably made the same particle size by classification.

The separating agent for enantiomeric isomers of the present invention is preferably used as a chiral stationary phase for chromatography such as gas chromatography, liquid chromatography, thin-layer chromatography, capillary electrophoresis or the like, and further preferably used as a liquid chromatographic chiral stationary phase or thin-layer chromatographic stationary phase used under a reversed phase condition, in particular under a reversed phase condition using a mobile phase formed of a single body of water, alcohol (methanol, ethanol, etc.) or acetonitrile or a mixture containing a plurality of liquids selected therefrom, an asymmetry recognition agent added to a migrating liquid or filled in a capillary in a capillary electrophoresis such as micelle dynamic chromatography, capillary electrochromatography or the like, and a stationary phase for continuous liquid preparative chromatography such as simulated moving bed process or the like. The mobile phases used under the reversed phase system condition include those containing a pH regulator (e.g., phosphoric acid, etc.), sodium perchlorate, potassium 6-fluorophosphate, or the like.

ADVANTAGE OF THE INVENTION

According to the present invention, a polysaccharide derivative-based asymmetry recognition agent with high asymmetry recognition ability and minimized UV absorption, that is suitably used as a HPLC chiral stationary phase under a reversed phase condition using an aqueous mobile phase or in chiral CE field, chiral TLC field and the like can be provided.

EXAMPLES

The present invention will be further described in more detail by way of examples. However, the present invention should not be construed as being limited to these examples. The capacity factor (k') and separation factor ($\alpha$) in the examples are defined by the following equations.

Capacity factor;

k'=[(Retention time of enantiomer)−(Dead time)]/(Dead time)

Separation Factor;

$\alpha$=(Capacity factor of more strongly absorbed enantiomer)/(Capacity factor of more weakly absorbed enantiomer)

The elution time of acetonitrile was taken as the dead time.

Example 1

Production of Cellulose Tris(cyclohexylcarboxylate)-Supported Filler and Packed Column (1) Synthesis of Cellulose Tris(cyclohexylcarboxylate) (a)

To 15 ml of N,N-dimethylacetamide (DMAc), 1.5 g of vacuum-dried lithium chloride was dissolved to prepare a DMAc/LiCl solution.

Under a nitrogen atmosphere, 15 ml of the above DMAc/LiCl solution and 15 ml of pyridine were added to 1.0 g of cellulose, and the resulting mixture was dipped in an oil bath at 100° C. and stirred for 24 hrs. Thereafter, 4.8 g of chloride cyclohexylcarboxylate ($C_6H_{11}COCl$) (34 mmol, 1.8 equivalents) was added thereto and reacted for 16 hrs at 100° C. The resulting solution was dripped in 200 ml of methanol and reprecipitated followed by centrifugal precipitation. As a result, the intended ester derivative (2.8 g, 93%) was obtained. The elemental analytic result of the resulting ester derivative (a) is shown in Table 1.

TABLE 1

| Elemental Analytic Result of Cellulose Tris(cyclohexylcarboxylate) (a) | | | |
|---|---|---|---|
| | C (%) | H (%) | N (%) |
| Calculated Value | 65.83 | 8.18 | 0.00 |
| Measured Value | 65.82 | 8.22 | 0.07 |

(2) Production of Filler with Cellulose Tris(cyclohexylcarboxylate) Supported Thereon To 10 ml of tetrahydrofuran (THF), 0.75 g of the ester derivative obtained in (1) was dissolved. The THF solution of the ester derivative was uniformly sprinkled on 3.0 g of silica gel treated with aminopropyl silane (particle size 7 μm, pore diameter 1000 Å), and the solvent was removed, whereby a filler with cellulose tris(cyclohexylcarboxylate) supported thereon was prepared.

(3) Production of Packed Column Using Cellulose Tris(cyclohexylcarboxylate)-Supported Filler The supported filler obtained in (2) was filled in a stainless column of ϕ0.46 cm×L25 cm with pressurizing by slurry filling method to form an enantiomeric isomer separation column.

Comparative Example 1

Production of Cellulose Triacetate-Supported Filler and Packed Column (1) Synthesis of Cellulose Triacetate Under a nitrogen atmosphere, 40 ml of acetic anhydride was added to 1.0 g of cellulose and reacted at 100° C. for 30 hrs. After the reaction, the resulting solution was allowed to stand cool to room temperature, and pored into 500 ml of methanol to precipitate cellulose triacetate. Glass filter filtration was then performed, and the filtrate was sufficiently washed with methanol and vacuum dried at 60° C. for 5 hrs.

As a result, the intended cellulose triacetate was obtained (1.69 g, Yield 95%).

(2) Production of Filler with Cellulose Triacetate Supported Thereon

To 10 ml of methylene chloride, 1.0 g of the cellulose triacetate obtained in (1) was dissolved. The resulting solution was uniformly sprinkled on 3.0 g of silica gel treated with aminopropyl silane (particle size 7 µm, pore diameter 1000 Å), and the solvent was removed, whereby a filler with cellulose triacetate supported thereon was produced.

(3) Production of Packed Column Using Cellulose Triacetate-Supported Filler

The supported filler formed in (2) was filled in a stainless column of φ0.46 cm×L25 cm with pressurizing by slurry filling method to prepare an enantiomeric isomer separation column for comparison.

Comparative Example 2

Production of Cellulose Tribenzoate-Supported Filler and Packed Column (1) Synthesis of Cellulose Tribenzoate Under a nitrogen atmosphere, 40 ml of pyridine was added to 1.0 g of cellulose, 6.5 g of benzoyl chloride was added thereto, and the mixture was reacted at 100° C. for 30 hrs. After the reaction, the resulting solution was allowed to stand cool to room temperature and poured into 500 ml of methanol to precipitate cellulose tribenzoate. Glass filter filtration was then performed, and the filtrate was sufficiently washed with methanol and vacuum dried at 60° C. for 5 hrs. As a result, the intended cellulose tribenzoate was obtained (2.49 g, Yield 85%).

(2) Production of Filler with Cellulose Tribenzoate Supported Thereon

To 10 ml of methylene chloride, 1.0 g of the cellulose tribenzoate obtained in (1) was dissolved. The resulting solution was uniformly sprinkled on 3.0 g of silica gel treated with aminopropyl silane (particle size 7 µm, pore diameter 1000 Å), and the solvent was removed, whereby a filler with cellulose tribenzoate supported thereon was prepared.

(3) Production of Packed Column Using Cellulose Tribenzoate-Supported Filler

The supported filler obtained in (2) was filled in a stainless column of φ0.46 cm×L25 cm with pressurizing by the slurry filling method to form an enantiomeric isomer separation column for comparison.

Applied Example 1

The enantiomeric isomer separation columns obtained in Example 1 and Comparative Examples 1–2 were used to perform the evaluation of asymmetry recognition ability for racemic modifications 1 and 2 represented by the following formulae by a liquid chromatography of the following condition. The result is shown in Table 2.

Liquid Chromatographic Condition

TABLE 2

| Mobile Phase | Example 1: $H_2O$/MeOH = 2.8 (v/v) |
| | Comparative Examples 1 and 2: MeOH |
| Flow Velocity | 0.5 ml/min |
| Temperature | 25° C. |

Racemic modification 1

Racemic modification 2

| | Separating Agent Separation Factor (α) | | |
|---|---|---|---|
| Racemic Modification | Example 1 | Comparative Example 1 | Comparative Example 2 |
| Racemic Modification 1 | 1.64 | 1.0 | 1.37 |
| Racemic Modification 2 | 1.16 | 1.0 | 1.0 |

Example 2

Production of Cellulose Tris(cyclopentylcarboxylate)-Supported Filler and Packed Column (1) Synthesis of Cellulose Tris(cyclopentylcarboxylate) (d)

To 15 ml of N,N-dimethylacetamide (DMAc), 1.5 g of vacuum-dried lithium chloride was dissolved to prepare a DMAc/LiCl solution.

Under a nitrogen atmosphere, 15 ml of the DMAc/LiCl solution and 15 ml of pyridine were added to 1.0 g of cellulose, and the mixture was dipped in a hot water bath at 100° C. and stirred for 24 hrs. Thereafter, 4.4 g of chloride cyclopentylcarboxylate (33 mmol, 1.8 equivalent) was added thereto and reacted at 100° C. for 16 hrs. The reaction dope was poured into 200 ml of MeOH and reprecipitated followed by centrifugal separation. As a result, the intended ester derivative was obtained (2.5 g, 90%). The elementary analytic result of (d) is shown in Table 3.

(2) Production of Filler with Cellulose Tris(cyclopentylcarboxylate) Supported Thereon To 10 ml of tetrahydrofurane (THF), 1.0 g of the ester derivative obtained in (1) was dissolved. The THF solution of the cellulose ester derivative was uniformly sprinkled on 3.0 g of silica gel treated with aminopropyl silane (particle size 7 µm, pore diameter 1000 Å), and the solvent was removed, whereby a filler with cellulose tris(cyclopentylcarboxylate) supported thereon was produced.

(3) Production of Packed Column Using Cellulose Tris(cyclopentylcarboxylate)-Supported Filler The supported filler obtained in (2) was filled in a stainless column of φ0.46 cm×L25 cm with pressurizing by the slurry filling method to prepare an enantiomeric isomer separation column.

Example 3

Production of Cellulose Tris(1-adamantylcarboxylate) Supported Filler and Packed Column (1) Synthesis of Cellulose Tris(1-adamantylcarboxylate) (e)

To 15 ml of N,N-dimethylacetamide (DMAc), 1.5 g of vacuum-dried lithium chloride 1.5 g was dissolved to prepare a DMAc/LiCl solution.

Under a nitrogen atmosphere, 15 ml of the DMAc/LiCl solution and 15 ml of pyridine were added to 1.0 g of cellulose, and the mixture was dipped in a hot water bath at 100° C. and stirred for 24 hrs. Thereafter, 9.2 g of chloride 1-adamantylcarboxylate (46 mmol, 2.5 equivalent) was added thereto and reacted at 100° C. for 48 hrs. The reaction dope was poured into 200 ml of MeOH and reprecipitated followed by centrifugal separation. As a result, the intended ester derivative was obtained (3.2 g, 80%). The elementary analytic result of (e) is shown in Table 3.

(2) Production of Filler with Cellulose Tris(1-adamantylcarboxylate) Supported Thereon To 10 ml of tetrahydrofurane (THF), 1.0 g of the ester derivative obtained in (1) was dissolved. The THF solution of the cellulose derivative was uniformly sprinkled on 3.0 g of silica gel treated with aminopropylsilane (particle size 7 µm, pore diameter 1000 Å), and the solvent was removed, whereby a filler with cellulose tris(1-adamantylcarobxylate) supported thereon was produced.

(3) Production of Packed Column Using Cellulose Tris(1-adamantylcarboxylate)-Supported Filler The supported filler obtained in (2) was filled in a stainless column of ϕ0.46 cm×L25 cm with pressurizing by the slurry filling method to prepare an enantiomeric isomer separation column.

TABLE 3

Elementary Analytic Result of Cellulose Tris(cyclopentylcarboxylate) and Cellulose Tris(1-adamantylcarboxylate)

|     |                  | C (%) | H (%) | N (%) |
|-----|------------------|-------|-------|-------|
| (d) | Calculated Value | 63.98 | 7.61  | 0.00  |
| (d) | Measured Value   | 63.45 | 7.51  | 0.04  |
| (e) | Calculated Value | 72.19 | 8.08  | 0.00  |
| (e) | Measured Value   | 69.50 | 7.97  | 0.11  |

Applied Examples 2 and 3

The enantiomeric isomer separation columns produced in Examples 2 and 3 were used to perform the evaluation of asymmetry recognition ability for the racemic modifications 1 and 2 used in Applied Example 1 by liquid chromatography in the same manner as in Applied Example 1. The result is shown in Table 4.

TABLE 4

Separation Factor α of Columns Formed in Examples 2 and 3

|                       | Separating Agent | |
|-----------------------|-----------|-----------|
| Racemic Modification  | Example 2 | Example 3 |
| Racemic Modification 1 | 1.34      | 1.19      |
| Racemic Modification 2 | 1.17      | 1.07      |

Analytic Condition: $H_2O$/MeOH = 2/8 (v/v); Flow Velocity 0.4 ml/min; Temperature 25° C.

What is claimed is:

1. A separating agent for enantiomeric isomers comprising a polysaccharide alicyclic ester derivative not having an aromatic group, said polysaccharide alicyclic ester derivative comprising a tris(cycloadamantylcarboxylate).

2. The separating agent for enantiomeric isomers according to claim 1, wherein the polysaccharide alicyclic ester derivative is a cellulose derivative.

3. A chiral stationary phase for chromatography comprising the separating agent of claim 1.

4. A chiral stationary phase for reversed phase liquid chromatography comprising the chiral stationary phase of claim 3.

5. A chiral stationary phase for thin-layer chromatography comprising the chiral stationary phase of claim 3.

6. An asymmetry recognition agent for capillary electrophoresis comprising the chiral stationary phase of claim 3.

7. A stationary phase for continuous liquid preparative chromatography comprising the chiral stationary phase of claim 3.

8. The separating agent for enantiomeric isomers according to claim 1, wherein the polysaccharide alicyclic ester derivative is an amylose derivative.

* * * * *